US008329214B2

(12) United States Patent
Stamm et al.

(10) Patent No.: US 8,329,214 B2
(45) Date of Patent: *Dec. 11, 2012

(54) PROCESS FOR PRODUCING FENOFIBRATE TABLETS

(75) Inventors: Andre Stamm, Griesheim (FR); Pawan Seth, Irvine, CA (US)

(73) Assignee: Laboratoires Fournier S.A., Dijon (FR)

( * ) Notice: Subject to any disclaimer, the term of this patent is extended or adjusted under 35 U.S.C. 154(b) by 209 days.

This patent is subject to a terminal disclaimer.

(21) Appl. No.: 11/723,646

(22) Filed: Mar. 21, 2007

(65) Prior Publication Data

US 2007/0190136 A1  Aug. 16, 2007

Related U.S. Application Data

(63) Continuation of application No. 10/665,520, filed on Sep. 22, 2003, now abandoned, which is a continuation of application No. 10/288,425, filed on Nov. 6, 2002, now Pat. No. 6,652,881, which is a continuation of application No. 10/126,875, filed on Apr. 22, 2002, now Pat. No. 6,589,552, which is a continuation of application No. 10/078,500, filed on Feb. 21, 2002, now Pat. No. 6,596,317, which is a continuation of application No. 09/899,026, filed on Jul. 6, 2001, now Pat. No. 7,037,529, which is a continuation of application No. 09/572,330, filed on May 18, 2000, now Pat. No. 6,277,405, which is a continuation of application No. 09/005,128, filed on Jan. 9, 1998, now Pat. No. 6,074,670, application No. 11/723,646, which is a continuation of application No. 10/290,333, filed on Nov. 8, 2002, now Pat. No. 7,041,319.

(30) Foreign Application Priority Data

Jan. 17, 1997 (FR) ...................................... 97 00479

(51) Int. Cl.
*A61K 9/66* (2006.01)
*A61K 9/48* (2006.01)
*A61K 9/14* (2006.01)

(52) U.S. Cl. ......... 424/455; 424/451; 424/452; 424/489

(58) Field of Classification Search .................. 424/464, 424/465
See application file for complete search history.

(56) References Cited

U.S. PATENT DOCUMENTS

| | | | |
|---|---|---|---|
| 2,953,497 A | 9/1960 | Press | |
| 4,344,934 A | 8/1982 | Martin et al. | |
| 4,412,986 A | 11/1983 | Kawata et al. | |
| 4,436,743 A | 3/1984 | Schonafinger et al. | |
| 4,524,060 A | 6/1985 | Mughal et al. | |
| 4,558,058 A | 12/1985 | Schonafinger et al. | |
| 4,629,624 A | 12/1986 | Grouiller et al. | |
| 4,663,150 A | 5/1987 | Panoz et al. | |
| 4,684,516 A | 8/1987 | Bhutani | |
| 4,716,033 A | 12/1987 | Denick, Jr. | |
| 4,717,569 A | 1/1988 | Harrison et al. | |
| 4,721,709 A | 1/1988 | Seth et al. | |
| 4,795,643 A | 1/1989 | Seth | |
| 4,800,079 A | 1/1989 | Boyer | |
| 4,806,361 A | 2/1989 | Harrison et al. | |
| 4,820,521 A | 4/1989 | Panoz et al. | |
| 4,895,726 A * | 1/1990 | Curtet et al. | |
| 4,925,672 A | 5/1990 | Gremm et al. | |
| 4,957,746 A | 9/1990 | Valducci | |
| 4,961,890 A | 10/1990 | Boyer | |
| 4,992,277 A | 2/1991 | Sangekar et al. | |
| 5,073,379 A | 12/1991 | Klimesch et al. | |
| 5,145,684 A | 9/1992 | Liversidge et al. | |
| 5,385,739 A | 1/1995 | Debregeas et al. | |
| 5,510,118 A * | 4/1996 | Bosch et al. | .................. 424/489 |
| 5,545,628 A | 8/1996 | Deboeck et al. | |
| 5,633,015 A | 5/1997 | Gilis et al. | |
| 5,776,495 A * | 7/1998 | Duclos et al. | |
| 5,783,215 A | 7/1998 | Arwidsson et al. | |
| 5,824,341 A | 10/1998 | Seth et al. | |
| 5,952,356 A * | 9/1999 | Ikeda et al. | |
| 6,027,747 A | 2/2000 | Terracol et al. | |
| 6,033,686 A | 3/2000 | Seth | |
| 6,042,847 A * | 3/2000 | Kerc et al. | |
| 6,048,547 A | 4/2000 | Seth et al. | |
| 6,074,670 A | 6/2000 | Stamm et al. | |
| 6,096,341 A | 8/2000 | Seth | |
| 6,117,453 A | 9/2000 | Seth et al. | |
| 6,159,499 A | 12/2000 | Seth | |
| 6,180,138 B1 | 1/2001 | Engh et al. | |
| 6,207,198 B1 | 3/2001 | Seth | |

(Continued)

FOREIGN PATENT DOCUMENTS

CA  960670  1/1975

(Continued)

OTHER PUBLICATIONS

Sheu et al., International Journal of Pharmaceutics, pp. 137-146, Mar. 15, 1994.
Guichard et al., "A New Formulation of Fenofibrate: Suprabioavailable Tablets," Current Medical Research & Opinion, vol. 16, No. 2, 2000, 134-138.
Temeljotov et al, Acta Pharm., 46:131-136 (1996).
Complaint, US District Court for the District of Delaware, Civil Action No. 04-350, *Reliant Pharmaceuticals v. Abbott Laboratories et al* (Jun. 1, 2004).
Opposition to EP 0 952 829 (Dec. 11, 2003) (English language translation).

(Continued)

*Primary Examiner* — Robert A Wax
*Assistant Examiner* — Jeffrey T Palenik
(74) *Attorney, Agent, or Firm* — Venable LLP; Keith G. Haddaway (57) ABSTRACT

The invention provides processes using suspensions to produce fenofibrate compositions. The resulting fenofibrate compositions can be made in the form of a tablet.

81 Claims, 2 Drawing Sheets

U.S. PATENT DOCUMENTS

| | | | |
|---|---|---|---|
| 6,248,355 | B1 | 6/2001 | Seth |
| 6,277,405 | B1 | 8/2001 | Stamm et al. |
| 6,348,469 | B1 | 2/2002 | Seth |
| 6,375,986 | B1 | 4/2002 | Ryde et al. |
| 6,444,225 | B1 | 9/2002 | Sherman |
| 6,589,552 | B2 | 7/2003 | Stamm et al. |
| 6,652,881 | B2 | 11/2003 | Stamm et al. |
| 7,037,529 | B2 | 5/2006 | Stamm et al. |
| 7,041,319 | B2 | 5/2006 | Stamm et al. |
| 7,276,249 | B2 | 10/2007 | Ryde et al. |
| 7,320,802 | B2 | 1/2008 | Ryde et al. |
| 2001/0006655 | A1 | 7/2001 | Chen et al. |
| 2002/0009496 | A1 | 1/2002 | Stamm et al. |
| 2002/0114839 | A1 | 8/2002 | Stamm et al. |
| 2002/0168413 | A1 | 11/2002 | Stamm et al. |
| 2003/0104051 | A1 | 6/2003 | Stamm et al. |
| 2003/0104060 | A1 | 6/2003 | Stamm et al. |
| 2004/0057997 | A1 | 3/2004 | Stamm et al. |
| 2004/0057998 | A1 | 3/2004 | Stamm et al. |
| 2004/0057999 | A1 | 3/2004 | Stamm et al. |
| 2004/0058004 | A1 | 3/2004 | Stamm et al. |
| 2004/0058005 | A1 | 3/2004 | Stamm et al. |
| 2004/0092597 | A1 | 5/2004 | Stamm et al. |
| 2005/0032878 | A1 | 2/2005 | Deboeck et al. |

FOREIGN PATENT DOCUMENTS

| | | |
|---|---|---|
| CA | 2142848 | 3/1994 |
| CA | 2219475 | 7/2002 |
| CA | 2372576 | 2/2004 |
| EP | 0 012 523 | 6/1980 |
| EP | 0 122 077 | 10/1984 |
| EP | 0 164 959 | 12/1985 |
| EP | 0 168 360 | 1/1986 |
| EP | 0 179 583 | 4/1986 |
| EP | 0 193 958 | 9/1986 |
| EP | 0 239 541 | 9/1987 |
| EP | 0 256 933 | 2/1988 |
| EP | 0 330 532 | 8/1989 |
| EP | 0 519 144 | 12/1992 |
| EP | 0 761 208 | 3/1997 |
| EP | 0 761 208 A1 | 3/1997 |
| EP | 0 793 958 | 9/1997 |
| EP | 0 256 933 | 2/1998 |
| EP | 0 952 829 | 3/2003 |
| EP | 0 952 829 B1 | 3/2003 |
| FR | 2758459 | 7/1998 |
| WO | WO 82/01649 | 5/1982 |
| WO | WO 96/01621 | 1/1996 |
| WO | WO 96/04892 | 2/1996 |
| WO | WO 96/21439 | 7/1996 |
| WO | WO 97/12580 | 4/1997 |
| WO | WO 97/12581 | 4/1997 |
| WO | WO 98/31360 | 7/1998 |
| WO | WO 98/31361 | 7/1998 |
| WO | WO 03/013500 | 2/2003 |

OTHER PUBLICATIONS

Opposition to EP 0 952 829 (Dec. 11, 2003) (original French language document).
Handbook of Pharmaceutical Excipients, Second Edition, pp. 392-399 (1994).
Laboratoires Fournier undated document entitled "Fenofibrate Tablets 54-160 mg Dissolution Test Conditions Development Studies, Dissolution Test Specification Recommendations", Rec'd by the Office on May 9, 2006.
"Second Amended Answer, Affirmative Defenses, and Counterclaims" filed by Teva on Jul. 29, 2005 in *Abbott Laboratories et al v. Teva Pharmaceuticals USA, Inc.* DE, CA No. 02-1512.
"First Amended Counterclaims" filed by Impax on Sep. 23, 2005 in *Abbott Laboratories et al v. Impax Laboratories, Inc.*, Delaware, CA No. 03-120-KAJ.
"Amended Complaint" filed by CVS Pharmacy et al on Sep. 23, 2005 in In Re TriCor Direct Purchaser Antitrust Litigation, Delaware, CA No. 05-340.
"Amended Complaint" filed by Walgreen Co. et al on Sep. 23, 2005 in In Re TriCor Direct Purchaser Antitrust Litigation, Delaware, CA No. 05-340.
"Amended Complaint" filed by Painters' District Council No. 30 et al on Sep. 23, 2005 in In Re TriCor Direct Purchaser Antitrust Litigation, Delaware, CA No. 05-340.
"Amended Complaint" filed by Louisiana Wholesale Drug Co. et al on Oct. 3, 2005 in In Re TriCor Direct Purchaser Antitrust Litigation, Delaware, CA No. 05-340.
"Defendant's Responses to Plaintiffs Interrogatories" filed by Impax on Aug. 6, 2003 in *Abbott Laboratories et al v. Impax Laboratories, Inc.*, Delaware, CA No. 03-120-KAJ.
"Amended Answer" filed by Impax on Jan. 4, 2005 in *Abbott Laboratories et al v. Impax Laboratories, Inc.*, Delaware, CA No. 03-120-KAJ.
"Reply Memorandum" filed by Impax on Feb. 25, 2005 in *Abbott Laboratories et al v. Impax Laboratories, Inc.*, Delaware, CA No. 03-120-KAJ.
"Memorandum Opinion" by District Judge Jordan dated May 6, 2005 in *Abbott Laboratories et al v. Impax Laboratories, Inc.*, Delaware, CA No. 03-120-KAJ.
"Opening Brief in Support of Motion for Summary Judgment" by Teva filed on Dec. 23, 2004 in *Abbott Laboratories et al v. Teva Pharmaceuticals USA, Inc.*, Delaware, CA No. 02-1512.
"Opening Brief in Support of Motion for Summary Judgment" by Teva filed on Dec. 10, 2004 in *Abbott Laboratories et al v. Teva Pharmaceuticals USA, Inc.*, Delaware, CA No. 02-1512.
"Memorandum Opinion" by District Judge Jordan dated May 6, 2005 in *Abbott Laboratories et al v. Teva Pharmaceuticals USA, Inc.*, Delaware, CA No. 02-1512.
Opposition to European Patent No. 1 273 293 filed Sep. 2, 2005 by Ethypharm (French Language Docuement).
Opposition to Israel Patent No. 130790 filed May 4, 2005 by Teva; and Remarks in Response to Oppostion filed on Sep. 23, 2005 (English language translations).
Munoz et al, Atherosclerosis, 110(Suppl.):S45-S48 (1994).
Pharmaceutical Pelletization Technology, Marcel Dekker, Inc., vol. 37, pp. 1-13; 160-161; and 234-235 (1989).
Modem Pharmaceutics, Third Edition, Marcel Dekker, Inc., apges 131-133 and 335-356 (1996).
Pharmaceutical Dosage Forms, Tablets, Second Edition, Marcel Dekker, Inc., pp. 5-28; 88-107; 133; 142; 160-165; and 260-267 (1989).
Shepherd Atherosclerosis, 110(Suppl.)S55-S63 (1994).
Adkins et al, Drugs, 54(4):615-633 (Oct. 1997).
Letter from Teva/Novopharm to Fournier Pharma Inc. regarding Invalidity and Ambiguity of Canadian Patent Nos. 2,219,475 and 2,372,576 (pp. 1-15)(Sep. 19, 2005).
Declaration under 37 CFR 1.132 by Phillippe Reginault filed in U.S. Appl. No. 10/288,425 on Mar. 7, 2005.
Pharmaceutical Pelletization Technology, Ghebre-Sallassie, Ed., Marcel Dekker, Inc., New York, Chapters 7 and 10 (1989).
Handbook of Pharmaceutical Excipients, 2nd Ed., pp. 48-87, 141-144, 229-232, 252-261, 280-282, 392-401, 424-427, 448-450, 462-469, 491-493 (1994).
Remington's Pharmaceutical Sciences, 18th Ed., pp. 1633-1665 (1985).
European Pharmacopoeia, 3rd Ed., pp. xiii-xvii and 127-131 (1996).
The United States Pharmacopoeia, vol. 23, pp. Iiv-Ivi, 1791-1793, 1924-1938 (1994).
CRC Handbook of Chemistry & Physics, 73rd Ed., Chapter 15, p. 32 (1992).
Suzuki et al, Chem. Pharm. Bull., 49(4):373-378 (2001).
Shah et al, International Journal of Pharmaceutics, 125:99-106 (1995).
Giunchedi et al, International Journal of Pharmaceutics, 130:41-47 (1996).
Sangalli et al, Boll. Chim. Farmaceutico, 128(7-8):242-247 (1989).
Kuchiki et al, "Stable Solid Dispersion System Against Humidity," Yakuzaigaku, 44(1):31-37 (1984).
Guichard et al, "A New Formulation of Fenofibrate: Suprabioavailable Tablets," Current Medical Research and Opinion, 16(2):134-138 (2000).

Boullay, "Microgrinding and Dissolution," S.T.P. Pharma, 1(4):296-299 (1985). (French-language document and English language translation).

International Dictionary of Medicine and Biology, vol. 2, p. 1774, John Wiley & Sons, Inc. (1986).

Opposition to EP 952 829 by Winthrop Arzneimitel GmbH filed Mar. 31, 2005.

Opposition to EP 952 829 by Laboratoires SMB SA filed Apr. 11, 2005.

Papers filed on Apr. 15, 2005, by Ethypharm in Response to Patent Proprietor's Statement of Opposition to EP 952 829.

Opposition to EP 0 952 829 by Ethypharm filed Dec. 11, 2003.

Declaration under 37 CFR 1.132 by Pascale Bloquin filed in U.S. Appl. No. 09/899,026 on Mar. 7, 2005.

Laboratoires Fournier's Lab Notebook No. 1 (attached as Exhibit 1 (French) and Exhibit 3 (English translation) to the 132 Declaration by Bloquin).

Laboratoires Fournier's Lab Notebook No. 2 (attaches as Exhibit 2 (French) and Exhibit 4 (English translation) to the 132 Declaration by Bloquin).

Notebook pp. dated Feb. 18 to May 15, 1997.

Notebook pp. dated May 16 to Jul. 30, 1997.

Opposition to European Patent No. 1 273 293 filed Sep. 2, 2005 by Ethypharm. (English Language Translation).

Laboratoires S.M.B. S.A. Report pp. 1-4 (undated), dated Sep. 13, 2005; rec'd by the Office Jun. 15, 2006.

Report from Pr. Rosset entitled "La biodisponibilite du fenofibrate et les polymeres hydrophiles," pp. 1-20 (Mar. 1, 2005).

\* cited by examiner

PROCESS FOR PRODUCING FENOFIBRATE TABLETS

RELATED APPLICATIONS

This application is a continuation of U.S. application Ser. No. 10/665,520 filed Sep. 22, 2003 now abandoned, which is a continuation of U.S. application Ser. No. 10/288,425 filed Nov. 6, 2002, issued as U.S. Pat. No. 6,652,881; which is a continuation of U.S. application Ser. No. 10/126,875 filed Apr. 22, 2002, issued as U.S. Pat. No. 6,589,552; which is a continuation of U.S. application Ser. No. 10/078,500 filed Feb. 21, 2002, issued as U.S. Pat. No. 6,596,317; which is a continuation of U.S. application Ser. No. 09/899,026 filed Jul. 6, 2001, issued as U.S. Pat. No. 7,037,529; which is a continuation of U.S. application Ser. No. 09/572,330 filed May 18, 2000, issued as U.S. Pat. No. 6,277,405; which is a continuation of U.S. application Ser. No. 09/005,128 filed Jan. 9, 1998, issued as U.S. Pat. No. 6,074,670; which claims priority to French Application No. 97 00 479 filed Jan. 17, 1997. This application is also a continuation of U.S. application Ser. No. 10/290,333 filed Nov. 8, 2002, issued as U.S. Pat. No. 7,041,319.

BACKGROUND OF THE INVENTION

The present invention relates to a novel pharmaceutical composition having high bioavailability through improved dissolution, and a method for preparing it. The invention more particularly relates to a pharmaceutical composition for administration by oral route, containing an active ingredient of poor aqueous solubility.

Numerous active ingredients suffer from the disadvantage of being poorly soluble in an aqueous medium, thus having an insufficient dissolution profile and, consequently, poor bioavailability within the organism, following oral administration. The therapeutic dose required to be administered must thus be increased in order to obviate this disadvantage. This particularly applies to numerous hypolipemiant active ingredients, such as those belonging to the fibrate family.

Fenofibrate is a well-known hypolipemiant from the family of fibrates, which is commercially available in various doses (100 and 300 mg for example Secalip®) but in a form leading to poor bioavailability of the active ingredient. Indeed, due to it poor hydrosolubility, fenofibrate is poorly absorbed in the digestive tract and consequently its bioavailability is incomplete, irregular and often varies from one person to another.

To improve the dissolution profile of fenofibrate and its bioavailability, thereby reducing the dose requiring to be administered, it would be useful to increase its dissolution so that it could attain a level close to 100%.

Moreover, for patient comfort, it is advantageous to seek a dosage form that only requires the medicament to be taken once daily while giving the same effect as one administered several times daily.

EP-A-0330532 discloses a method for improving bioavailability of fenofibrate. This patent describes the effect of co-micronizing fenofibrate with a surfactant, for example sodium laurylsulfate in order to improve fenofibrate solubility and thereby increase its bioavailability. This patent teaches that co-micronizing fenofibrate with a solid surfactant improves fenofibrate bioavailability to a much greater extent than the improvement that would be obtained either by adding a surfactant, or through solely micronizing the fenofibrate, or, yet again, through intimately mixing the fenofibrate and surfactant, micronized separately. The dissolution method employed is the conventional rotating blade technique (European Pharmacopoeia): product dissolution kinetics are measured in a fixed volume of the dissolution medium, agitated by means of a standardized device; a test was also carried out with an alternative technique to the European Pharmacopoeia, using the continuous-flow cell method.

The process of EP-A-0330532 leads to a new dosage form in which the active ingredient, co-micronized with a solid surfactant, has improved fenofibrate dissolution, and thus increased bioavailability, which makes it possible, for a given level of effectiveness, to decrease the daily dose of the medicament: respective 67 mg and 200 mg instead of 100 mg and 300 mg.

However, the preparation method in that patent is not completely satisfactory inasmuch as it does not lead to complete bioavailability of the active ingredient, and suffers from several disadvantages. The technique of co-micronizing fenofibrate with a solid surfactant does, it is true, improve dissolution of the active ingredient, but this dissolution remains, however, incomplete.

There is thus a need to improve fenofibrate bioavailability in order to attain, over very short periods of time, a level close to 100% (or, in any case, better than the following limits: 10% in 5 minutes, 20% in 10 minutes, 50% in 20 minutes and 75% in 30 minutes in a medium consisting of 1200 ml water to which 2% Polysorbate 80 is added, or of 1000 ml of water to which 0.025 M sodium lauryl sulfate sodium is added, with a blade rotation speed of 75 rpm), and this even when dissolution media having a low surfactant content are used.

Applicant has found that, surprisingly, it is possible to resolve this problem by a new method for preparing a pharmaceutical composition by spraying a suspension of the active ingredient onto an inert hydrosoluble carrier. The present invention also relates to pharmaceutical compositions thus prepared.

The use is already known of a polymer, such as polyvinylpyrrolidone for producing tablets, in concentrations of the order of 0.5 to 5% by weight, at a maximum 10% by weight. In this case, the polyvinylpyrrolidone is used as a binder. Similarly, the use of a polymer such as hydroxymethylpropylmethyl cellulose as a granulation binder is known. Thus, European patent application 0,519,144 discloses pellets of a poorly soluble substance, omeprazole, obtained by spraying a dispersion or suspension of the active ingredient in a solution containing said polymer onto inert pellets in a fluidized-bed granulator. However, here again, the polymer (HPMC and HPC) is only used as a granulation binder, in an amount of about 50% by weight, based on the weight of the active ingredient, which, bearing in mind the presence of the inert pellets of a large size (about 700 μm) and the overall final weight leads to final active ingredient and polymer contents which are very low, of the order of barely a few percent based on the weight of the final covered pellet. Finally, it will be noted that the size of the inert pellets in this documents is fairly large, which, in the case of fenofibrate, would lead to a final formulation having a volume which is much too large for ready oral administration.

The use of polymer, such as polyvinylpyrrolidone for manufacturing "solid dispersions" is also known, obtained in general by co-precipitation, co-fusion or liquid-phase mixing followed by drying. What we have here is fixation of the active ingredient in isolated microparticles on the polyvinylpyrrolidone, which avoids problems of poor wetting of the solid and re-agglomeration of the particles. The article "Stable Solid Dispersion System Against Humidity" by Kuchiki et al., Yakuzaigaku, 44 No. 1, 31-37 (1984) describes such a technique for preparing solid dispersions using polyvinylpyrrolidone. The amounts of PVP here are very high, and the ratio between the active ingredient and PVP are comprised between 1/1 and 1/20. In the case however there is no inert carrier.

WO-A-96 01621 further discloses a sustained release composition, comprising an inert core (silica in all examples) coated with a layer which contains the active ingredient in admixture with a hydrophilic polymer, the weight ratio active ingredient/polymer being comprised between 10/1 and 1/2 and the weight ratio active ingredient/inert core being comprised between 5/1 and 1/2, with an outer layer to impart the sustained release property. These compositions can be compressed. The hydrophilic polymer can be polyvinylpyrrolidone. This document also discloses a process for preparing said composition; for example in a fluidized-bed granulator one will spray a dispersion of active ingredient in a polymer solution onto the inert cores. This document solely relates to sustained release compositions, the technical problem to be solved being the compression, without damages, of the outer layer imparting the sustained release property.

Nevertheless, nothing in the state of the art teaches nor suggest the present invention.

SUMMARY OF THE INVENTION

Thus, the present invention provides an immediate-release fenofibrate composition comprising:

(a) an inert hydrosoluble carrier covered with at least one layer containing a fenofibrate active ingredient in a micronized form having a size less than 20 μm, a hydrophilic polymer and, optionally, a surfactant; said hydrophilic polymer making up at least 20% by weight of (a); and (b) optionally one or several outer phase(s) or layer(s).

In one embodiment, a surfactant is present with the active ingredient and the hydrophilic polymer.

The invention also provides a composition comprising fenofibrate having a dissolution of at least 10% in 5 minutes, 20% in 10 minutes, 50% in 20 minutes and 75% in 30 minutes, as measured using the rotating blade method at 75 rpm according to the European Pharmacopoeia, in a dissolution medium constituted by water with 2% by weight polysorbate 80 or in a dissolution medium constituted by water with 0.025 M sodium lauryl sulfate.

A method for preparing a pharmaceutical composition is also provided, comprising the steps of:

(a) preparing a fenofibrate suspension in micronized form with a particle size below 20 μm, in a solution of hydrophilic polymer and, optionally surfactant;

(b) applying the suspension from step (a) to an inert hydrosoluble carrier;

(c) optionally, coating granules thus obtained with one or several phase(s) or layer(s).

Step (b) is preferably carried out in a fluidized-bed granulator.

The method can comprise a step in which products obtained from step (b) or (c) are compressed, with or without additional excipients.

The invention also provides a suspension of fenofibrate in micronized form having a size less than 10 μm, in a solution of hydrophilic polymer and, optionally, surfactant.

The invention will be described in more detail in the description which follows, with reference to the attached drawings.

DETAILED DESCRIPTION OF PREFERRED EMBODIMENTS

The expression "in micronized form" in this invention means a substance in a particulate form, the dimensions of the particles being less than or equal to about 20 μm.

Advantageously, this dimension is less than or equal to 10 μm.

In the framework of this invention, the expression "inert hydrosoluble carrier" means any excipient, generally hydrophilic, pharmaceutically inert, crystalline or amorphous, in a particulate form, not leading to a chemical reaction under the operating conditions employed, and which is soluble in an aqueous medium, notably in a gastric acid medium. Examples of such excipients are derivatives of sugars, such as lactose, saccharose, hydrolyzed starch (malto-dextrine), etc. Mixture are also suitable. The individual particle size of the inert hydrosoluble carrier can be, for example, between 50 and 500 micron.

The expression "hydrophilic polymer" in the invention should be taken to mean any high molecular weight substance (greater, for example, than 300) having sufficient affinity towards water to dissolve therein and form a gel. Examples of such polymers are polyvinylpyrrolidone, poly(vinyl alcohol), hydroxypropylcellulose, hydroxymethylcellulose, hydroxypropylmethylcellulose, gelatin, etc. Polymer blends are also suitable.

The preferred hydrophilic polymer is polyvinylpyrrolidone (PVP). The PVP used in this invention has, for example, a molecular weight comprised between 10,000 and 100,000, preferably for example between 20,000 and 55,000.

The term "surfactant" is used in its conventional sense in this invention. Any surfactant is suitable, whether it be amphoteric, non-ionic, cationic or anionic. Examples of such surfactants are: sodium lauryl sulfate, monooleate, monolaurate, monopalmitate, monostearate or another ester of polyoxyethylene sorbitane, sodium dioctylsulfosuccinate (DOSS), lecithin, stearylic alcohol, cetostearylic alcohol, cholesterol, polyoxyethylene ricin oil, polyoxyethylene fatty acid glycerides, Poloxamer®, etc. Mixtures of surfactants are also suitable.

The preferred surfactant is sodium laurylsulfate, which can be co-micronized with fenofibrate.

The compositions according to the invention can additionally contain any excipient conventionally used in the pharmaceutical and chemical fields which is compatible with the active ingredient, such as binders, fillers, pigments, disintegrating agents, lubricants, wetting agents, buffers, etc. As examples, excipients able to be used in this invention we can cite: microcrystalline cellulose, lactose, starch, colloidal silica, talc, glycerol esters, sodium stearyl fumarate, titanium dioxide, magnesium stearate, stearic acid, cross-linked polyvinyl pyrrolidone (AC DI SOL®), carboxymethyl starch (Explotab®, Primojel®), hydroxypropylcellulose, hydroxymethylcellulose, hydroxypropylmethylcellulose, gelatin, etc.

Here, the expression "outer phase or layer" should be taken to mean any coating on the element (a) with the active ingredient (forming a "core"). Indeed, it can be useful to have available one or several phase(s) or layer(s) on top of the coated core. The invention thus covers a single core with one layer, but also several cores in a phase, as is the case of tablets which are formed from "cores" mixed with a phase.

This outer layer comprises conventional excipients.

It is also possible to provide a layer comprising additives, for the manufacture of tablets. In this embodiment, the outer layer comprises a disintegration agent and, for example, a lubricant; the thus covered and mixed granules can then be readily compressed and easily disintegrate in water.

The compositions according to the invention comprise, in general, based on the total composition weight excluding the outer phase or layer, an inert hydrosoluble carrier making up from 10 to 80% by weight, preferably 20 to 50% by weight, the fenofibrate representing from 5 to 50% by weight, preferably from 20 to 45% by weight, the hydrophilic polymer representing from 20 to 60% by weight, preferably 25 to 45% by weight, the surfactant making up from 0 to 10% by weight, preferably 0.1 to 3% by weight.

The outer layer or phase if present, can make up to 80% by weight of the total weight, preferably up to 50% by weight.

The hydrophilic polymer represents preferably more than 25% by weight, based on the weight of (a).

The weight ratio of fenofibrate/hydrophilic polymer can for example be comprised between 1/10 and 4/1, preferably, for example, between 1/2 and 2/1.

When a surfactant is employed, the weight ratio surfactant/hydrophilic polymer can be comprised for example between 1/500 and 1/10, preferably, for example, between 1/100 and 5/100.

In one embodiment, the composition according to the invention takes the form of tablets.

This tablet preferably results from the compression of elements (a) (under the form of granules) together with an outer phase.

In another embodiment, the composition of the invention takes the form of granules enclosed inside a capsule, for example in gelatin, or inside a bag.

The compositions of the invention are particularly suitable for administering active ingredients by oral route.

The composition according to the invention is prepared by a novel process comprising spraying a suspension of the active ingredient in a micronized form in a solution of a hydrophilic polymer and, optionally, a surfactant, onto the inert core.

When a surfactant is present, the active ingredient can be co-micronized with the surfactant. One will then use with advantage the teachings of EP-A-0330532.

The method according to the invention consists in using the fluidized bed granulation principle, but with specific starting materials, in order to arrive at an improved dissolution profile and thus, at elevated bioavailability. In particular, the invention employs a suspension of the micronized active ingredient in a solution of a hydrophilic polymer and, optionally, a surfactant.

The fluidized-bed granulation technique is widely used in the pharmaceutical industry for preparing capsules or tablets. Conventionally, according to the prior art, a powder or a mixture of powders (active ingredient+excipients) is put into suspension in the fluidized bed in a granulator, and a solution containing a binder and, optionally, a surfactant, is sprayed onto this bed to form granules. The fluidized-bed granulation technique is well known to those skilled in the art and reference should be made to standard works such as for example "Die Tablette", by Ritschel, Ed. Cantor Aulendorf, pages 211-212.

The invention, as has been indicated, comprises spraying a suspension of an active ingredient micronized with a hydrophilic polymer onto an inert carrier. Following granulation, the granulate formed consists of crystals of, for example, lactose, which are isolated (or possibly agglomerated together by the spray solution) and particles of active ingredient and PVP adhering to the crystal surface. The granule could similarly be constituted of coated crystals which are agglomerated, or even of such an agglomerate having received a coating.

The compositions according to the invention can also be prepared by other methods, for example by spraying a solution of the micronized active ingredient onto the hydrosoluble inert carrier.

The granulates thus obtained can, if desired, be provided with an outer coating or compressed into tablets, or form agglomerates.

The outer layer or layer is/are applied using conventional coating techniques such as coating in a pan or fluidized bed coater.

When the granulate obtained (whether subsequently coated or not) is compressed to form tablets, this step can be implemented using any conventional technique which is suitable, for example using an alternating or rotating compressing equipment.

The significant starting product is the suspension of the active ingredient. This suspension is prepared by putting the micronized active ingredient into suspension in a solution comprising the hydrophilic polymer and, optionally, a surfactant, in solution in a solvent. If a surfactant is employed, it is put into solution in the solvent (beaker+magnetic or vane stirrer). Next, the hydrophilic polymer (PVP) is dispersed, while stirring, in the solution previously obtained. Depending on polymer solubility, this either dissolves in the solution or forms a gel or a suspension having varying degrees of thickness. While still stirring, the micronized active ingredient is dispersed in the form of a fine shower into the above solution or suspension, to form a homogeneous suspension. The order of these steps can be reversed. The solvent employed can be aqueous or organic (for example ethanol). For example demineralized water can be used.

The active ingredient concentration in the suspension is from 1 to 40% by weight, preferably from 10 to 25%.

The hydrophilic polymer concentration in the suspension is from 5 to 40% by weight, preferably 10 to 25%.

The surfactant concentration in the suspension is from 0 to 10% by weight, preferably below 5%.

The invention also covers this novel suspension.

Without wishing to be tied down to a specific theory, applicant believes that this novel method, through the use of a micronized active ingredient suspension in a hydrophilic polymer solution, enabled a novel composition to be obtained in which the active ingredient is in a non-re-agglomerated form.

The following examples illustrate the invention without limiting it.

Example 1

Preparation of a pharmaceutical composition of fenofibrate according to the invention.

A composition containing, as the element a), micronized fenofibrate, Plasdone®, Capsulac® and sodium lauryl sulfate was prepared.

The micronized fenofibrate had a particle size of about 5 μm, as measured using a Coulter counter.

The Plasdone K25® corresponds to a polyvinylpyrrolidone PVP ISP and the Capsulac 60® corresponds to a coarse crystal lactose monohydrate (Meggle) (particle size between 100 and 400 μm).

The sodium laurylsulfate (7 g) is dissolved in water (demineralized water, 1750 g) and the micronized fenofibrate (350 g) is put into suspension in the mixture obtained (for example using a helix stirrer at 300 rpm for 10 minutes, then using an Ultra Turrax agitator at 10,000 rpm, for 10 minutes). Following this, the PVP (350 g) is added while still agitating, stirring (helix stirrer) being continued until the latter had dissolved (30 minutes). It is all passed through a sieve (350 µm) to eliminate possible agglomerates.

Separately, the lactose (400 g) is put into suspension in a fluidized air bed granulator (of the Glatt® GPCG1—Top Spray type or equivalent) and heated to a temperature of 40° C.

The fenofibrate suspension is sprayed onto the lactose. This step is carried out under the following conditions: spraying pressure: 2.1 bar, air throughput 70 m³/h, air inlet temperature: 45° C.; air outlet temperature: 33° C.; product temperature 34° C.; duration of spraying: 3 h.

The granulate thus obtained can be put inside capsules or transformed into tablets. Any suitable conventional technique for preparing such dosage forms can be used.

For transformation to tablet form, one will mix 191 g of the granulate obtained (using for example a mixer-grinder type mixing apparatus, a planetary mixer or turn-over mixer), with the outer phase having the following composition:

56 g Polyplasdone XL® (cross-linked polyvinylpyrrolidone ISP, as described in the USA Pharmacopoeia "USP-NF" under the name of crospovidone, mean molecular weight>1,000,000);

88 g Avicel® PH200 (microcrystalline cellulose);

3.5 g sodium stearyl fumarate (Mendell, U. S. A.); and 2 g Aerosil® 200 (colloidal silica).

The cross-linked polyvinylpyrrolidone, the microcrystalline cellulose, the sodium stearyl fumarate and the colloidal silica are respectively, disintegration agents, binders, lubricating and flow enhancing agents.

The tablet can be obtained on an alternating compression machine (for example Korsch EKO) or a rotary machine (for example Fette Perfecta 2).

One thus obtains tablets having the following composition, expressed in mg:

element (a):

|   |   |
|---|---|
| micronized fenofibrate | 100.0 |
| PVP | 100.0 |
| Lactose | 114.3 |
| sodium laurylsulfate | 2.0 | outer phase (or layer):

|   |   |
|---|---|
| cross-linked PVP | 92.7 |
| microcrystalline cellulose | 145.7 |
| sodium stearyl fumarate | 5.8 |
| colloidal silica | 3.3 |

Example 2

Dissolution of a composition according to the invention and a composition according to the prior art.

a) Dissolution Medium and Procedure for Measuring Dissolution.

A dissolution medium which is discriminating, in other words one in which two products having very different dissolution profiles in gastric juices will have very different dissolution curves is looked for.

For this, an aqueous medium containing a surfactant, this being Polysorbate 80 (polyoxyethylene sorbitane mono-oleate) is used. This surfactant is readily available from various suppliers, is the object of a monograph in the Pharmacopoeias, and is thus easy to implement (being also a water-soluble liquid product). Other surfactants can also be used.

The rotating blade method (European Pharmacopoeia) is used under the following conditions: volume of medium: 1200 ml; medium temperature: 37° C.; blade rotation speed: 75 rpm; samples taken: every 2.5 minutes. Determination of the amount dissolved is carried out by spectrophotometry. Test are repeated 6 times over.

b) Results

The composition according to the invention consisted of two tablets containing about 100 mg fenofibrate prepared according to Example 1.

The prior art composition was Lipanthyl® 200 M from Laboratories Fournier, containing 200 mg fenofibrate (corresponding to capsules of 200 mg fenofibrate, co-micronized with sodium laurylsulfate, and containing lactose, pre-gelatinized starch, cross-linked polyvinylpyrrolidone and magnesium stearate, in line with the teachings of EP-A-0330532).

Figure 1:
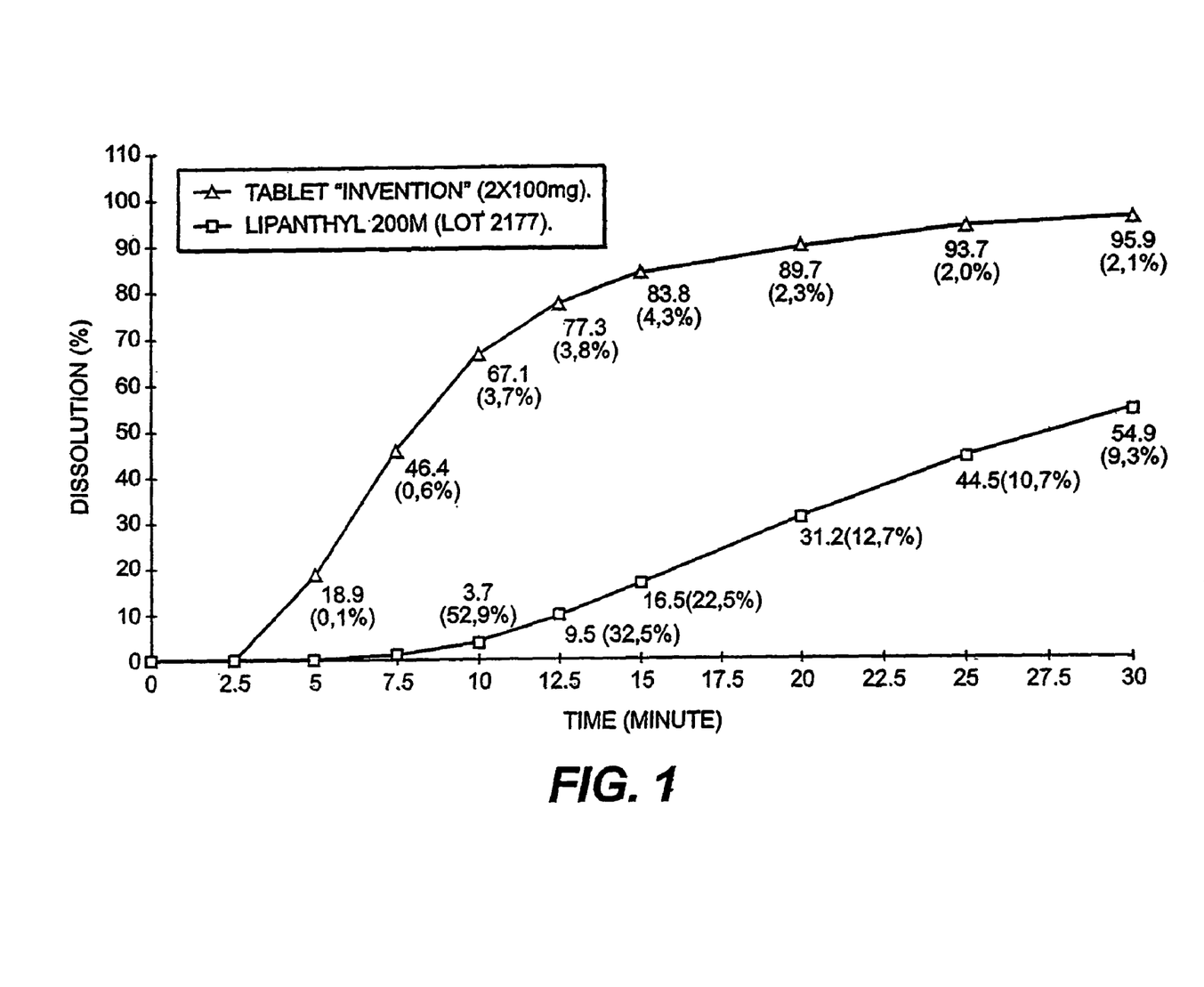
FIG. 1 is a graph of a comparative study of the dissolution profile of a composition according to the invention, compared to that of Lipanthyl® 200 M.

The results obtained are shown graphically in FIG. 1, on which the percentage of dissolution is shown, the observed standard deviation being indicated between brackets.

These results clearly show that the compositions according to the invention have a dissolution profile which is distinctly better than that of the prior art compositions.

These results also clearly show that with the compositions of the invention, the standard deviation observed is distinctly lower than is the case with prior art compositions.

Example 3

Study of bioavailability of compositions according to the invention and prior art compositions.

A test of bioavailability on healthy volunteers was carried out.

The following compositions were tested:

composition according to the invention: capsules containing granules prepared according to example 1, containing 200 mg fenofibrate.

first composition according to the prior art: Lipanthyl® 200 M from Laboratories Fournier, containing 200 mg fenofibrate, identical to that in the previous example.

second prior art composition: Secalip® in capsule form (300 mg fenofibrate in the form of three 100 mg capsules).

The study was carried out on 6 healthy volunteers receiving a single dose of fenofibrate, with a minimum 6-day rest period between administrations. The samples for pharmaco-kinetic analysis were collected after each administration at the following times: 0.5 h; 1 h; 2 h; 3 h; 4 h; 5 h; 6 h; 8 h; 10 h; 12 h; 24 h; 36 h; 48 h; 72 h; and 96 hours following administration of the medicament. Fenofibric acid content in plasma was measured for each sample.

The results obtained are given in table 1 below.

TABLE 1

| Product | dose (mg) | Cmax (μg/ml) | tmax (h) | t½ (h) | AUC 0-t (μg · h/ml) | AUC 0-∞ (μg · h/ml) |
|---|---|---|---|---|---|---|
| Invention | 200 | 5.4 | 6 | 23 | 148 | 162 |
| Secalip ® 100 | 3 × 100 | 1.1 | 25 | 39 | 53 | 56 |
| Lipanthyl ® 200M | 200 | 1.6 | 8.3 | 41 | 71 | 92 |

Cmax: maximum plasma concentration
tmax: time to reach Cmax
t½: plasma halflife
AUC 0-t: area under the curve from 0 to t
AUC 0-∞: area under the curve from 0 to ∞.

The results clearly show that the compositions of the present invention have a dissolution profile that is an improvement over compositions of the prior art, leading to a considerably enhanced bioavailability of the active ingredient compared to that obtained with compositions of the prior art.

Example 4

Comparison of the dissolution profile of compositions according to the invention and that of products currently on the German market.

Figure 2:
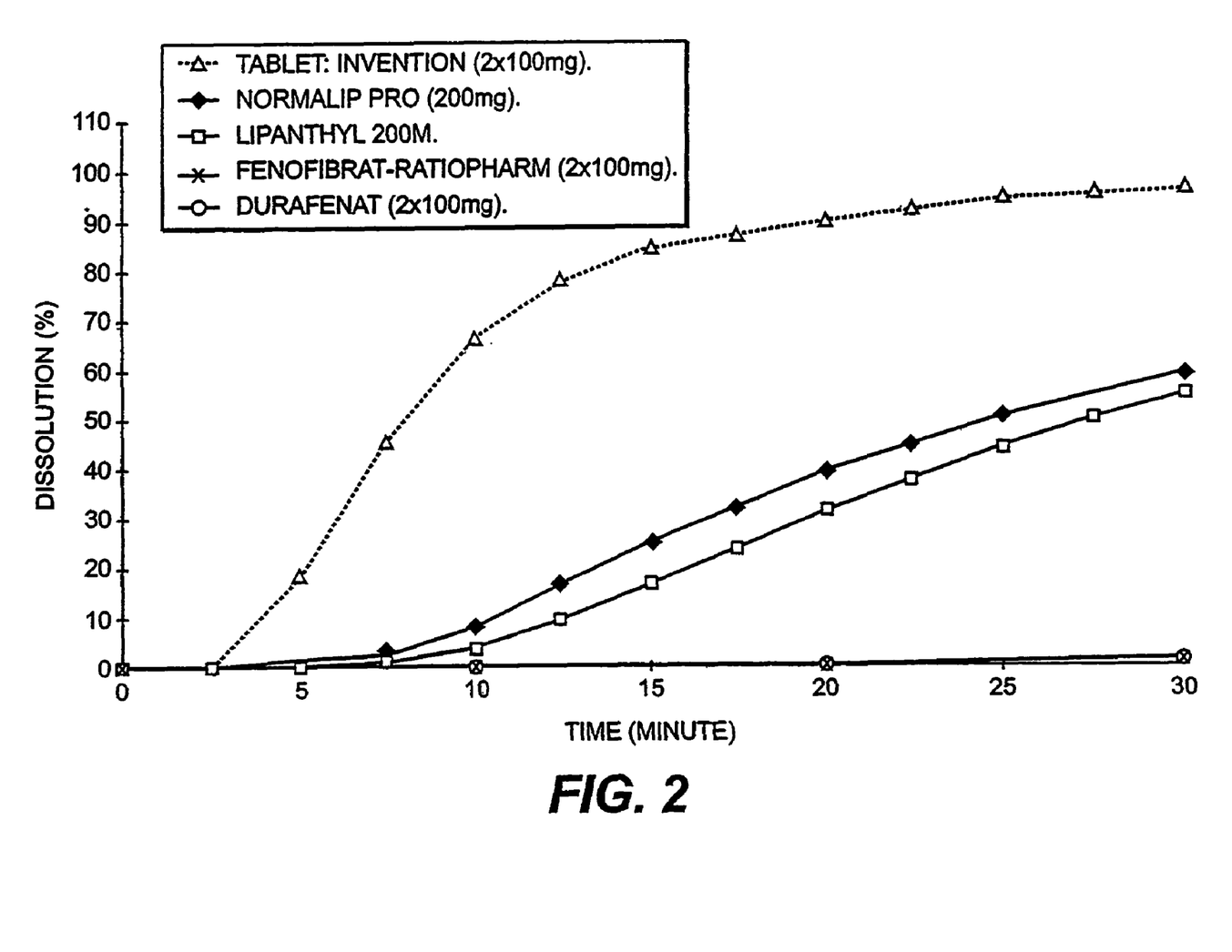
FIG. 2 is a graph illustrating a comparative study of the dissolution profile of a composition according to the invention and that of pharmaceutical products commercially available on the German market.

On the German market, immediate or sustained-release fenofibrate formulations exist. Like in France, the 100 mg and 300 mg (conventional) forms coexist with 67 and 200 mg forms (having enhanced bioavailability, according to the teaching of EP-A-0330532). These products are as follows:

Fenofibrate—ratiopharm; Ratiopharm—Ulm;
Capsules;
Composition: 100 mg fenofibrate;
Excipients: lactose, corn starch, magnesium stearate, E 171 colorant, gelatine.
Durafenat; Durachemie—Wolfratshausen Capsules;
Composition: 100 mg fenofibrate;
Excipients: lactose, corn starch, magnesium stearate, E 171 colorant, gelatine.
Normalip pro; Knoll—Ludwigshafen;
Capsules;
Composition: 200 mg Fenofibrate;
Excipients: Crospovidone, gelatine, monohydrate lactose, magnesium stearate, corn starch, sodium laurylsulfate, E 132 and E 171 colorants.
A comparison was made between:
the tablet of the invention as prepared using example 1 (2×100 mg)
Normalip Pro® (200 mg);
Lipanthyl® 200 M (200 mg) (according to the preceding example);
Fenofibrate by Ratiopharm® (2×100 mg);
Durafenat® (2×100 mg)
The tests were implemented under the same conditions as in the previous examples. FIG. 2 summarizes the results.

These results clearly show that the compositions of the invention have a distinctly improved dissolution compared to prior art compositions.

Obviously, the present invention is not limited to the embodiments described but may be subject to numerous variations readily accessible to those skilled in the art.

What is claimed is:

1. A process for producing a tablet comprising micronized fenofibrate, wherein the process comprises:
    (i) preparing an aqueous suspension comprising at least one hydrophilic polymer wherein one of the hydrophilic polymers is polyvinylpyrrolidone with a molecular weight between 20,000 and 100,000; and micronized fenofibrate particles having a particle size of less than 20 μm;
    (ii) spraying the suspension onto inert carriers to form granulates; and
    (iii) compressing the granulates to form the tablet.

2. The process of claim 1, wherein step (i) of preparing the suspension comprises (a) preparing a solution comprising at least one hydrophilic polymer and (b) adding the fenofibrate to the solution to produce the suspension.

3. The process of claim 1, wherein step (i) of preparing the suspension comprises (a) preparing a solution comprising at least one hydrophilic polymer by dissolving the hydrophilic polymer and (b) adding the fenofibrate to the solution to produce the suspension.

4. The process of claim 1, wherein step (i) of preparing the suspension comprises (a) adding the fenofibrate to a solution to form the suspension, and (b) dissolving at least one hydrophilic polymer in the suspension.

5. The process of claim 1, wherein the suspension further comprises at least one surfactant.

6. The process of claim 1, wherein the suspension comprises fenofibrate and hydrophilic polymer in a weight ratio of fenofibrate/hydrophilic polymer between 1/10 and 4/1.

7. The process of claim 1, wherein the suspension comprises fenofibrate and hydrophilic polymer in a weight ratio of fenofibrate/hydrophilic polymer between 1/2 and 2/1.

8. The process of claim 1, wherein the fenofibrate has a particle size less than 10 μm.

9. The process of claim 1, wherein the suspension comprises fenofibrate in an amount from 1 to 40% by weight.

10. The process of claim 9, wherein the suspension comprises fenofibrate in an amount from 10 to 25% by weight.

11. The process of claim 1, wherein the suspension comprises the hydrophilic polymer in an amount from 5 to 40% by weight.

12. The process of claim 11, wherein the suspension comprises the hydrophilic polymer in an amount from 10 to 25% by weight.

13. The process of claim 1, wherein the hydrophilic polymer further comprises a poly(vinyl alcohol), a hydroxypropylcellulose, a hydroxy-methylcellulose, a hydroxypropylmethylcellulose, a gelatin, or a mixture of two or more thereof.

14. The process of claim 5, wherein the suspension comprises the surfactant in an amount of up to 10% by weight.

15. The process of claim 14, wherein the suspension comprises the surfactant in an amount of up to 5% by weight.

16. The process of claim 5, wherein the suspension comprises surfactant and hydrophilic polymer in a weight ratio of surfactant/hydrophilic polymer between 1/500 and 1/10.

17. The process of claim 5, wherein the suspension comprises surfactant and hydrophilic polymer in a weight ratio of surfactant/hydrophilic polymer between 1/100 and 5/100.

18. The process of claim 5, wherein the surfactant is sodium lauryl sulfate, monooleate, monolaurate, monopalmitate, monostearate or another ester of polyoxyethylene sorbitane, sodium dioctylsulfosuccinate, lecithin, stearylic alcohol, cetostearylic alcohol, cholesterol, polyoxyethylene ricin oil, polyoxyethylene fatty acid glycerides, poloxamer, or a mixture of two or more thereof.

19. The process of claim 18, wherein the surfactant is sodium lauryl sulfate.

20. The process of claim 1, wherein the inert carriers are inert hydrosoluble carriers.

21. The process of claim 1, which further comprises, between steps (ii) and (iii), mixing the granulates with at least one pharmaceutical excipient.

22. The process of claim 21, wherein said pharmaceutical excipient is selected from the group consisting of at least one binder, at least one filler, at least one pigment, at least one disintegrating agent, at least one lubricant, at least one wetting agent, at least one buffer, and a mixture of two or more thereof.

23. The process of claim 21, wherein said pharmaceutical excipient is selected from the group consisting of microcrystalline cellulose, lactose, starch, colloidal silica, talc, glycerol esters, sodium stearyl fumarate, titanium dioxide, magnesium stearate, stearic acid, cross-linked polyvinyl pyrrolidone, carboxymethyl starch, hydroxypropylcellulose, hydroxymethylcellulose, hydroxypropylmethylcellulose, gelatin, and a mixture of two or more thereof.

24. A process for producing a tablet comprising micronized fenofibrate, wherein the process comprises:
   (i) preparing an aqueous suspension comprising at least one surfactant, at least one hydrophilic polymer wherein one of the hydrophilic polymers is polyvinylpyrrolidone with a molecular weight between 20,000 and 100,000; and micronized fenofibrate particles having a particle size of less than 20 µm;
   (ii) spraying the aqueous suspension onto inert carriers to form granulates; and
   (iii) compressing the granulates to form the tablet.

25. The process of claim 24, wherein step (i) of preparing the aqueous suspension comprises (a) preparing an aqueous solution comprising at least one surfactant and at least one hydrophilic polymer and (b) adding the fenofibrate to the aqueous solution to produce the aqueous suspension.

26. The process of claim 24, wherein step (i) of preparing the aqueous suspension comprises (a) preparing an aqueous solution comprising at least one surfactant and at least one hydrophilic polymer by dissolving the surfactant and hydrophilic polymer and (b) adding the fenofibrate to the aqueous solution to produce the aqueous suspension.

27. The process of claim 24, wherein step (i) of preparing the aqueous suspension comprises (a) dissolving at least one surfactant in an aqueous solution, (b) dissolving at least one hydrophilic polymer in the aqueous solution, and (c) adding the micronized fenofibrate to the aqueous solution to produce the aqueous suspension.

28. The process of claim 24, wherein step (i) of preparing the aqueous suspension comprises (a) dissolving at least one hydrophilic polymer in an aqueous solution, (b) dissolving at least one surfactant in an aqueous solution, and (c) adding the fenofibrate to the aqueous solution to form the aqueous suspension.

29. The process of claim 24, wherein step (i) of preparing the aqueous suspension comprises (a) dissolving at least one surfactant in an aqueous solution, (b) adding the fenofibrate to the aqueous solution to form the aqueous suspension, and (c) dissolving at least one hydrophilic polymer in the aqueous suspension.

30. The process of claim 24, wherein step (i) of preparing the aqueous suspension comprises (a) dissolving at least one hydrophilic polymer in an aqueous solution, (b) adding the fenofibrate to the aqueous solution to form the aqueous suspension, and (c) dissolving at least one surfactant in the aqueous suspension.

31. The process of claim 24, wherein the suspension comprises fenofibrate and hydrophilic polymer in a weight ratio of fenofibrate/hydrophilic polymer between 1/10 and 4/1.

32. The process of claim 24, wherein the suspension comprises fenofibrate and hydrophilic polymer in a weight ratio of fenofibrate/hydrophilic polymer between 1/2 and 2/1.

33. The process of claim 24, wherein the fenofibrate has a particle size less than 10 µm.

34. The process of claim 24, wherein the suspension comprises fenofibrate in an amount from 1 to 40% by weight.

35. The process of claim 24, wherein the suspension comprises fenofibrate in an amount from 10 to 25% by weight.

36. The process of claim 24, wherein the suspension comprises the hydrophilic polymer in an amount from 5 to 40% by weight.

37. The process of claim 24, wherein the suspension comprises the hydrophilic polymer in an amount from 10 to 25% by weight.

38. The process of claim 24, wherein the hydrophilic polymer further comprises a poly(vinyl alcohol), a hydroxypropylcellulose, a hydroxy-methylcellulose, a hydroxypropylmethylcellulose, a gelatin, or a mixture of two or more thereof.

39. The process of claim 24, wherein the suspension comprises the surfactant in an amount of up to 10% by weight.

40. The process of claim 39, wherein the suspension comprises the surfactant in an amount of up to 5% by weight.

41. The process of claim 24, wherein the suspension comprises surfactant and hydrophilic polymer in a weight ratio of surfactant/hydrophilic polymer between 1/500 and 1/10.

42. The process of claim 24, wherein the suspension comprises surfactant and hydrophilic polymer in a weight ratio of surfactant/hydrophilic polymer between 1/100 and 5/100.

43. The process of claim 24, wherein the surfactant is sodium lauryl sulfate, monooleate, monolaurate, monopalmitate, monostearate or another ester of polyoxyethylene sorbitane, sodium dioctylsulfosuccinate, lecithin, stearylic alcohol, cetostearylic alcohol, cholesterol, polyoxyethylene ricin oil, polyoxyethylene fatty acid glycerides, poloxamer, or a mixture of two or more thereof.

44. The process of claim 43, wherein the surfactant is sodium lauryl sulfate.

45. The process of claim 24, wherein the inert carriers are inert hydrosoluble carriers.

46. The process of claim 24, which further comprises, between steps (ii) and (iii), mixing the granulates with at least one pharmaceutical excipient.

47. The process of claim 46, wherein said pharmaceutical excipient is selected from the group consisting of at least one binder, at least one filler, at least one pigment, at least one disintegrating agent, at least one lubricant, at least one wetting agent, at least one buffer, and a mixture of two or more thereof.

48. The process of claim 46, wherein said pharmaceutical excipient is selected from the group consisting of microcrystalline cellulose, lactose, starch, colloidal silica, talc, glycerol esters, sodium stearyl fumarate, titanium dioxide, magnesium stearate, stearic acid, cross-linked polyvinyl pyrrolidone, carboxymethyl starch, hydroxypropylcellulose, hydroxymethylcellulose, hydroxypropylmethylcellulose, gelatin, and a mixture of two or more thereof.

49. A process for producing a tablet comprising micronized fenofibrate, wherein the process comprises:
   (i) preparing an aqueous suspension comprising at least one surfactant, at least one hydrophilic polymer wherein one of the hydrophilic polymers is polyvinylpyrrolidone with a molecular weight between 20,000 and 100,000; and micronized fenofibrate particles having a particle size of less than 20 µm; by (a) preparing an aqueous solution comprising at least one surfactant and at least one hydrophilic polymer by dissolving said surfactant and hydrophilic polymer and (b) adding the fenofibrate particles to the solution to produce the aqueous suspension;

(ii) spraying the aqueous suspension onto inert carriers to form granulates; and (iii) compressing the granulates to form the tablet.

50. The process of claim 49, wherein the suspension comprises fenofibrate and hydrophilic polymer in a weight ratio of fenofibrate/hydrophilic polymer between 1/10 and 4/1.

51. The process of claim 49, wherein the suspension comprises fenofibrate and hydrophilic polymer in a weight ratio of fenofibrate/hydrophilic polymer between 1/2 and 2/1.

52. The process of claim 49, wherein the fenofibrate has a particle size less than 10 µm.

53. The process of claim 49, wherein the suspension comprises fenofibrate in an amount from 1 to 40% by weight.

54. The process of claim 53, wherein the suspension comprises fenofibrate in an amount from 10 to 25% by weight.

55. The process of claim 49, wherein the suspension comprises the hydrophilic polymer in an amount from 5 to 40% by weight.

56. The process of claim 55, wherein the suspension comprises the hydrophilic polymer in an amount from 10 to 25% by weight.

57. The process of claim 49, wherein the hydrophilic polymer further comprises a poly(vinyl alcohol), a hydroxypropylcellulose, a hydroxy-methylcellulose, a hydroxypropylmethylcellulose, a gelatin, or a mixture of two or more thereof.

58. The process of claim 49, wherein the suspension comprises the surfactant in an amount of up to 10% by weight.

59. The process of claim 58, wherein the suspension comprises the surfactant in an amount of up to 5% by weight.

60. The process of claim 49, wherein the suspension comprises surfactant and hydrophilic polymer in a weight ratio of surfactant/hydrophilic polymer between 1/500 and 1/10.

61. The process of claim 49, wherein the suspension comprises surfactant and hydrophilic polymer in a weight ratio of surfactant/hydrophilic polymer between 1/100 and 5/100.

62. The process of claim 49, wherein the surfactant is sodium lauryl sulfate, monooleate, monolaurate, monopalmitate, monostearate or another ester of polyoxyethylene sorbitane, sodium dioctylsulfosuccinate, lecithin, stearylic alcohol, cetostearylic alcohol, cholesterol, polyoxyethylene ricin oil, polyoxyethylene fatty acid glycerides, poloxamer, or a mixture of two or more thereof.

63. The process of claim 62, wherein the surfactant is sodium lauryl sulfate.

64. The process of claim 49, wherein the inert carriers are inert hydrosoluble carriers.

65. The process of claim 49, which further comprises, between steps (ii) and (iii), mixing the granulates with at least one pharmaceutical excipient.

66. The process of claim 65, wherein said pharmaceutical excipient is selected from the group consisting of at least one binder, at least one filler, at least one pigment, at least one disintegrating agent, at least one lubricant, at least one wetting agent, at least one buffer, and a mixture of two or more thereof.

67. The process of claim 65, wherein said pharmaceutical excipient is selected from the group consisting of microcrystalline cellulose, lactose, starch, colloidal silica, talc, glycerol esters, sodium stearyl fumarate, titanium dioxide, magnesium stearate, stearic acid, cross-linked polyvinyl pyrrolidone, carboxymethyl starch, hydroxypropylcellulose, hydroxymethylcellulose, hydroxypropylmethylcellulose, gelatin, and a mixture of two or more thereof.

68. The process of claim 1, wherein the tablet comprises from 5 to 50% by weight of fenofibrate, from 10 to 75% by weight of carrier, and from 20 to 60% by weight of hydrophilic polymer.

69. The process of claim 68, wherein the tablet comprises from 20 to 45% by weight fenofibrate, from 20 to 50% by weight carrier, and from 25 to 45% by weight hydrophilic polymer.

70. The process of claim 68, wherein the tablet further comprises up to 10% by weight surfactant.

71. The process of claim 70, wherein the tablet further comprises from 0.1 to 3% by weight surfactant.

72. The process of claim 24, wherein the tablet comprises from 5 to 50% by weight fenofibrate, from 10 to 75% by weight carrier, from 20 to 60% by weight hydrophilic polymer, and up to 10% by weight surfactant.

73. The process of claim 72, wherein the tablet comprises from 20 to 45% by weight fenofibrate, from 20 to 50% by weight carrier, from 25 to 45% by weight hydrophilic polymer, and from 0.1 to 3% by weight surfactant.

74. The process of claim 49, wherein the tablet comprises from 5 to 50% by weight fenofibrate, from 10 to 75% by weight carrier, from 20 to 60% by weight hydrophilic polymer, and up to 10% by weight surfactant.

75. The process of claim 74, wherein the tablet comprises from 20 to 45% by weight fenofibrate, from 20 to 50% by weight carrier, from 25 to 45% by weight hydrophilic polymer, and from 0.1 to 3% by weight surfactant.

76. The process of claim 1, wherein step (ii) is fluidized bed granulation.

77. The process of claim 24, wherein step (ii) is fluidized bed granulation.

78. The process of claim 49, wherein step (ii) is fluidized bed granulation.

79. The process of claim 1, wherein said tablet is an immediate release tablet.

80. The process of claim 24, wherein said tablet is an immediate release tablet.

81. The process of claim 49, wherein said tablet is an immediate release tablet.

* * * * *